United States Patent
Zhao et al.

(10) Patent No.: US 6,649,778 B1
(45) Date of Patent: Nov. 18, 2003

(54) METHODS OF PREPARING AMINO ACID TAXANE DERIVATIVES AND POLYMER CONJUGATES CONTAINING THE SAME

(75) Inventors: Hong Zhao, Edison, NJ (US); Richard B. Greenwald, Somerset, NJ (US)

(73) Assignee: Enzon, Inc., Bridgewater, NJ (US)

( * ) Notice: Subject to any disclaimer, the term of this patent is extended or adjusted under 35 U.S.C. 154(b) by 0 days.

(21) Appl. No.: 10/252,024

(22) Filed: Sep. 20, 2002

(51) Int. Cl.[7] .............................................. C07D 305/14
(52) U.S. Cl. ........................ 549/510; 549/511; 525/403
(58) Field of Search ................. 549/510, 511; 525/403

(56) References Cited

U.S. PATENT DOCUMENTS 4,960,790 A    10/1990    Stella et al. ................. 514/449

OTHER PUBLICATIONS

Mathew, Abraham E., et al. Synthesis and Evaluation of Some Water–Soluble Prodrugs and Derivatives of Taxol with Antitumor Activity, J. Med. Chem. 1992, 35, 145–151.
Carpino, Louis A., et al. The 1,1–Dioxobenzo–beta–thiophene–2–ylmethyloxycarbonyl (Bsmoc) Amino–Protecting Group, J. Org. Chem. 1999, 64 4324–4338.
Zhao Zhiyang, et al. et al. Modified Taxols, 6, Preparation of Water–Soluble Prodrugs of Taxol, Journal of Natural Products, vol. 54, No. 6, pp. 1607–1611, Nov.–Dec. 1991.

Primary Examiner—Ba K. Trinh

(74) Attorney, Agent, or Firm—Muserlian, Lucas & Mercanti, LLP

(57) ABSTRACT

Methods of preparing amino acid-substituted taxanes such as:

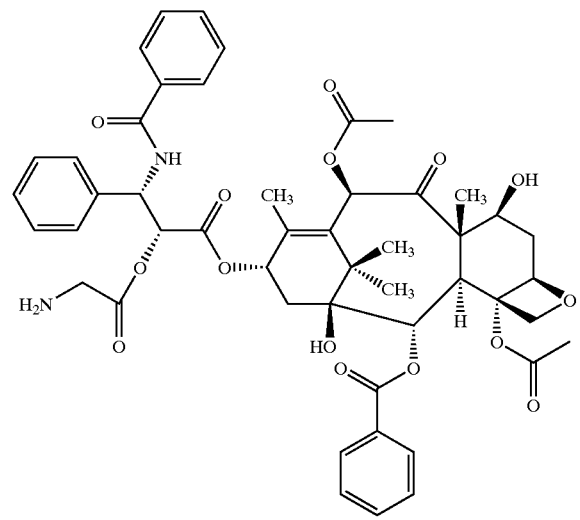

using selected blocked amino acids are disclosed. After coupling of the blocked amino acid to the taxane, deprotection is carried out with about an equimolar amount of a secondary amine thus substantially avoiding base-catalyzed hydrolysis of amino acid from the taxane. The preferred amino acid-taxanes are useful as intermediates in the production of polymer conjugated therapeutic compositions or as part of pharmaceutically acceptable formulations.

23 Claims, 2 Drawing Sheets

METHODS OF PREPARING AMINO ACID TAXANE DERIVATIVES AND POLYMER CONJUGATES CONTAINING THE SAME

FIELD OF INVENTION

The present invention relates to methods of selectively derivatizing taxanes such as paclitaxel at the 2'-position thereof with amino acids and the like. The invention also relates to polymer conjugates made therewith.

BACKGROUND OF THE INVENTION

Various plant alkaloids such as the vinka derivatives vinblastine and vincristine, camptothecin and paclitaxel have been shown to have potent anti-cancer effects. Such alkaloids are often poorly soluble. Indeed, because paclitaxel is so poorly soluble, the commercially available formulation for injection or I.V. infusion includes the solubilizer Cremophore EL. Cremophore, however, can be toxic. It is associated with idiosyncratic histamine release and anaphylactic reactions. Alternatives have therefore been sought.

One solution to improve solubility has been to provide amino acid derivatives of the desired anticancer alkaloids. For example, U.S. Pat. No. 4,943,579 discloses certain amino acid derivatives of camptothecin as having improved water solubility. The camptothecin is first converted to the chloroacetate using chloroacetic anhydride, pyridine and DMAP. The chloroacetate is then converted to the iodoacetate before being finally converted into the amino acid ester using a secondary amine. The stability of the final product, (a salt thereof) is only reported in terms of hydrolysis in plasma.

Amino acid derivatives of paclitaxel have also been disclosed. See, for example, U.S. Pat. No. 4,960,790 to Stella, et al., which discloses various 2'- and 7-protected amino acid paclitaxels. According to Stella, the reaction of the alkylated or protected amino acid is conducted in the presence of a condensing reagent, optionally with a catalyst, preferably at room temperature. Mentioned condensing reagents include carbodiimides, such as dicyclohexyl carbodiimide (DCC), while the catalysts mentioned include 4-dimethylamino-pyridine (DMAP) and pyridine. More importantly, the amino acid protecting groups employed include t-BOC, Fmoc or carbobenzyloxy (CBZ). Degradation of the final product and stereochemical modification are observed during deprotection. The problem is especially troublesome when synthesizing 2'-gly-paclitaxel. Deprotecting the 2'-gly-paclitaxel under acidic conditions makes purification and recovery of the free 2'-gly-paclitaxel almost impossible because of decomposition.

The use of formic acid to deprotect 2'-t-Boc amino acid taxanes has also been suggested. Shortcomings, however, have been associated with process as well. See, Mathew, A., et al. "Synthesis and Evaluation of Some Water-Soluble Prodrugs and Derivatives of Taxol With Antitumor Activity", *J. Med. Chem.* 1992, 35, 145–151. First, the 2'-amino acid paclitaxel is produced in low yield, and a complicated purification must be employed for isolation. In addition, substantially complete rapid decomposition of the 2'-gly-paclitaxel derivative was still observed. Thus, further improvements are desirable.

Another process for providing 2'-amino acid paclitaxel derivatives includes using Fmoc protected amino acids. Acceptable yields of the 2'-amino acid paclitaxels are obtained after the protecting group is removed with an excess of piperidine. Although the free amino acid derivative is formed in the piperidine-containing mixture, substantial decomposition occurs during purification and isolation. The problem is particularly observed in the case of synthesizing 2'-gly-derivative.

A further refinement of the 2'-amino acid taxane synthesis proposed deblocking the Fmoc protecting group with DMAP rather than with piperidine at elevated temperature. While this has reduced the decomposition of the free 2'-amino acid taxane somewhat, further improvements have been sought.

Carpino et al. in *J. Am. Chem. Soc.* 1997, (119) pp 9915–9916, disclose the use of 1,1-dioxobenzo[b]thiophene-2-ylmethoxycarbonbyl (hereinafter "Bsmoc") as an alternative to Fmoc in peptide synthesis. Deprotection of Bsmoc amino acids allows the concurrent scavenging of the beta elimination products. There is no disclosure or suggestion of using the reagent in a process for attaching an amino acid or peptide to taxane derivatives, or that deprotecting of 2'-Bsmoc-amino acid taxanes with secondary amines could reduce or even overcome the problems associated with the use of other protected amino acids and deprotecting reagents.

In view of the foregoing, there is still a need for improving the processes employed for making stable amino acid esters of taxanes. The present invention addresses this need.

SUMMARY OF THE INVENTION

In one aspect of the invention, there is provided a method of preparing a 2'-substituted taxanes such as paclitaxel. The method includes:

a) reacting a taxane of the formula (I)

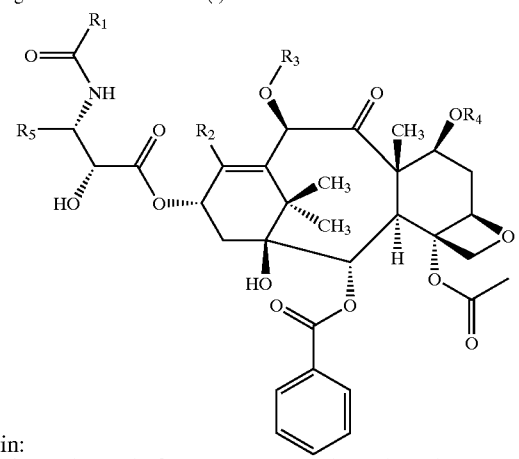

(I)

wherein:
$R_1$ is selected from among phenyl, t-butoxy, isopropyloxy, propyloxy, —C(CH$_3$)=CH—CH$_3$, 2-naphthyl, 4-hydroxyphenyl, 4-methoxyphenyl, 4-fluorophenyl, 2-methyl-1-propenyl, cyclopropyl, 3-furanyl, 3-thioethyl and 2-propenyl;
$R_2$ is one of acetyl, —CH$_3$, —CH$_2$CH$_3$ and —CHO;
$R_3$ is selected from among acetyl, H and C$_{1-6}$ alkyl;
$R_4$ is selected from among H, F, C$_{1-6}$ alkyl, —C(O)—CH$_2$CH$_2$CH$_2$CH$_2$CH$_3$, —CH$_2$SCH$_3$, —SiEt$_3$, —CH$_2$OP(O)(OCH$_2$Ph)$_2$, CH$_3$CH$_2$C(O)—, —CH$_2$O(CO)CH$_2$N(CH$_2$CH$_2$)$_2$NCH$_3$, —CH$_2$O(CO)CH$_2$N(CH$_2$CH$_3$)$_2$, —C(O)CH$_2$N(CH$_3$)$_2$, —C(O)CH(CH$_3$)NHCOOC(CH$_3$)$_3$; and
$R_5$ is selected from among phenyl, 4-methoxyphenyl, 3,4-dimethoxyphenyl, 4-fluorophenyl, 4-trifluorotoluene, 2-furanyl, 2-thienyl, phenylethene, 2-furanyl-CH=CH—, (CH$_3$)$_2$CHCH$_2$—, C$_6$H$_{11}$—CH$_2$—, (CH$_3$)$_2$CH—, PhCH$_2$CH$_2$—, C$_6$H$_{11}$—CH$_2$CH$_2$—, CH$_3$CH$_2$CH$_2$—, 4—Cl-phenyl-, 2-fluorophenyl-, 3-fluoro-phenyl- and 4-CH$_3$-phenyl- with a compound of formula (II)

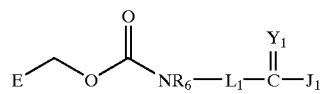 (II)

wherein:

E is selected from among

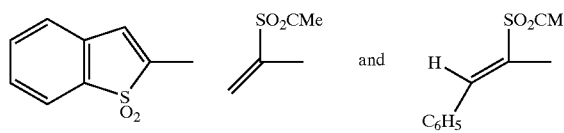 and

L$_1$ is a bifunctional group;
Y$_1$ is selected from among O, S or NR$_7$;
R$_6$ and R$_7$ are independently selected from among hydrogen, C$_{1-6}$ alkyls, C$_{3-19}$ branched alkyls, C$_{3-8}$ cycloalkyls, C$_{1-6}$ substituted alkyls, C$_{3-8}$ substituted cycloalkyls, aryls, substituted aryls, aralkyls, C$_{1-6}$ heteroalkyls, substituted C$_{1-6}$ heteroalkyls, C$_{1-6}$ alkoxy, phenoxy and C$_{1-6}$ heteroalkoxy; and
J$_1$ is OH or a leaving group;
under conditions sufficient to form a blocked intermediate of the formula (III)

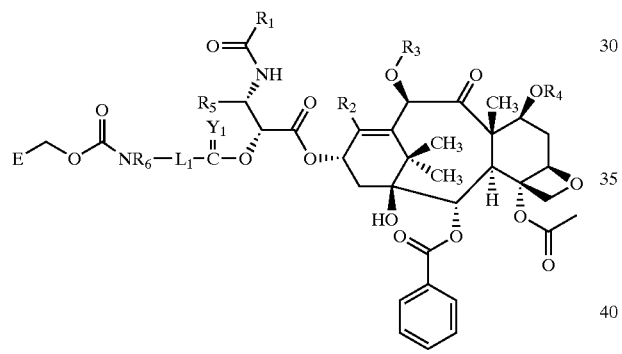

b) deprotecting the blocked intermediate with about an equimolar amount of a secondary amine, such as piperidine or 4-piperidinopiperidine, under conditions sufficient to form a compound of formula (IV):

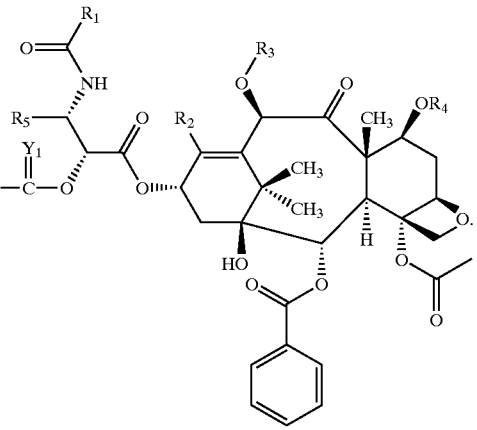

Another aspect of the invention includes reacting a compound of formula (IV), in situ, if desired, with an activated polymer of formula (Va):

R$_8$—(L$_2$)$_d$—C(=Y$_2$)—J$_2$ or (Vb) J$_2$—C(=Y$_2$)—(L$_2$)$_d$—R$_8$—(L$_2$)$_d$—C(=Y$_2$)—J$_2$ to form a polymer conjugate of formula (VIa):

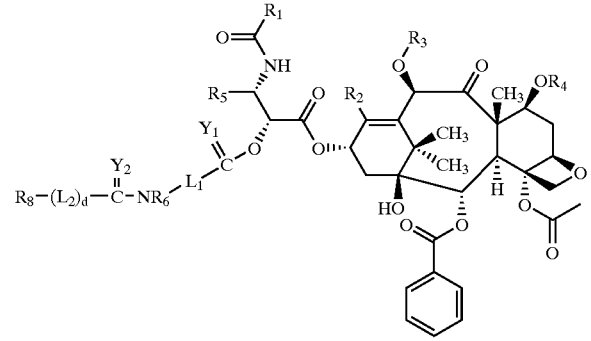

or formula (VIb):

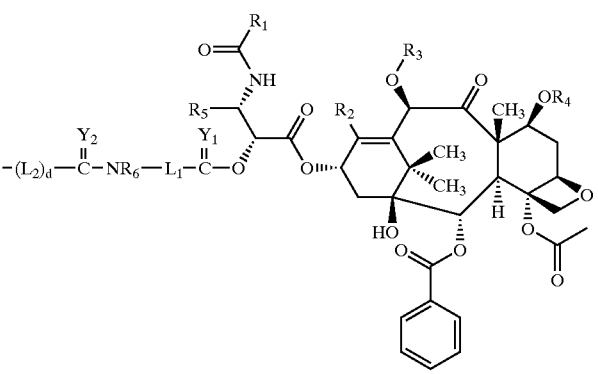

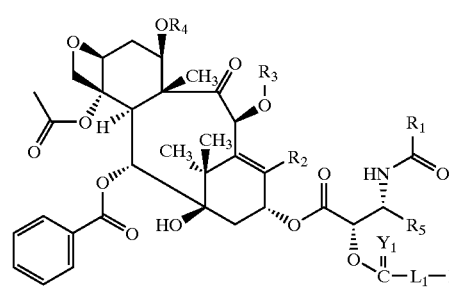

wherein
R$_8$ is a residue of a substantially non-antigenic polymer;
L$_2$ is a bifunctional linker selected from among the same members of the group which comprise L$_1$;
Y$_2$ is selected from among O, S and R$_{7a}$ where R$_{7a}$ is selected from the same group which defines R$_7$;
d is zero or one; and
J$_2$ is OH or a leaving group.

In preferred aspects of this embodiment, the activated polymers are either mono- or bis PEG-CO$_2$H.

The polymer conjugates can be used in the treatment of various taxane-sensitive conditions known to those of ordinary skill.

For purposes of the present invention, "mild conditions" shall be understood to include, inter alia, temperatures around room temperature, short reaction times of about 1–2 hours, and non-molar excess of deprotective reagents.

For purposes of the present invention, the term "residue" shall be understood to mean that portion of a compound, to which it refers, that remains after it has undergone a substitution reaction in which the polymeric prodrug carrier portion has been attached.

For purposes of the present invention, the term "polymeric residue" or "PEG residue" shall each be understood to mean that portion of the polymer or PEG which remains after it has undergone a reaction with a biologically active compound.

For purposes of the present invention, the term "alkyl" shall be understood to include straight, branched, substituted, e.g. halo-, alkoxy-, nitro-, C$_{1-12}$ alkyls, C$_{3-8}$ cycloalkyls or substituted cycloalkyls, etc.

For purposes of the present invention, the term "substituted" shall be understood to include adding or replacing one or more atoms contained within a functional group or compound with one or more different atoms.

For purposes of the present invention, substituted alkyls include carboxyalkyls, aminoalkyls, dialkylaminos, hydroxyalkyls and mercaptoalkyls; substituted alkenyls include carboxyalkenyls, aminoalkenyls, dialkenylaminos, hydroxyalkenyls and mercaptoalkenyls; substituted alkynyls include carboxyalkynyls, aminoalkynyls, dialkynylaminos, hydroxyalkynyls and mercaptoalkynyls; substituted cycloalkyls include moieties such as 4-chlorocyclohexyl; aryls include moieties such as napthyl; substituted aryls include moieties such as 3-bromo-phenyl; aralkyls include moieties such as toluyl; heteroalkyls include moieties such as ethylthiophene; substituted heteroalkyls include moieties such as 3-methoxy-thiophene; alkoxy includes moieties such as methoxy; and phenoxy includes moieties such as 3-nitrophenoxy. Halo- shall be understood to include fluoro, chloro, iodo and bromo.

The term "sufficient amounts" for purposes of the present invention shall mean an amount which achieves a therapeutic effect as such effect is understood by those of ordinary skill in the art.

For purposes of the present invention, "effectively non-antigenic" and "substantially non-antigenic" shall be understood to include all polymeric materials understood in the art as being substantially non-toxic and not eliciting an appreciable immune response in mammals.

For purposes of the present invention, a "positive integer" shall be understood to mean a positive whole number, preferably from about 1 to 6 and more preferably 1 or 2.

As a result of the present invention, there are provided improved processes for preparing amino acid esters of taxanes. The compounds made with the process of the present invention find utility, for example as pharmacological agents and as important intermediates in the formation of 2'-taxane polymer conjugates. The use of Bsmoc and related amino-protecting groups allow the artisan to form stable 2'-substituted taxane end products in high yield and in economical fashion. The use of Bsmoc protected amino acids allows the artisan to make 2'-protected amino acid taxanes in relatively high yields with minimal purification being required. Without wishing to be bound by theory, the desired products are obtained with minimal degradation because the Bsmoc deprotection of the amino acid taxane can be achieved under mild conditions with about an equimolar, rather than excess, amount of the secondary amine base. These conditions allow the desired free amino acid taxane to be isolated and recovered in quantitative yields and minimal decomposition.

A further advantage of using the Bsmoc-based processes of the present invention is the fact that the deprotection reaction acts simultaneously as a scavenging reaction to remove the Beta elimination product. Thus, purification and even in situ PEGylation are quite economical when compared to prior art techniques. Other and further advantages will be apparent to those of ordinary skill in view of the following description and appended claims.

DETAILED DESCRIPTION OF THE INVENTION

Figure 1:
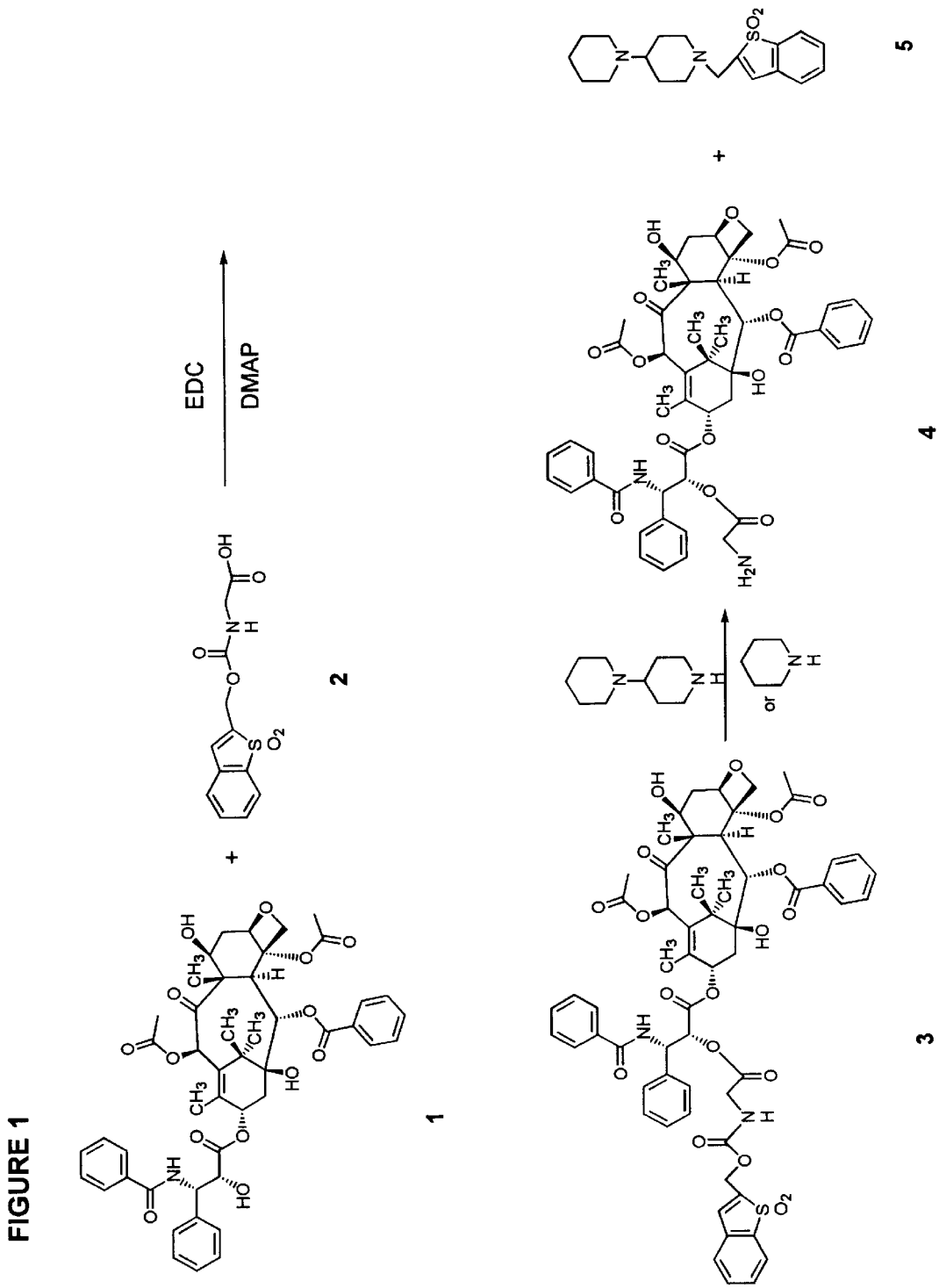
FIGS. 1–2 schematically illustrate methods of forming compounds of the present invention which are described in the detailed description and examples.

In certain preferred aspects of the invention, methods of preparing 2'-substituted taxanes are provided. Although there are various taxanes which have demonstrated various therapeutic properties, preferred taxanes include those of formula (I):

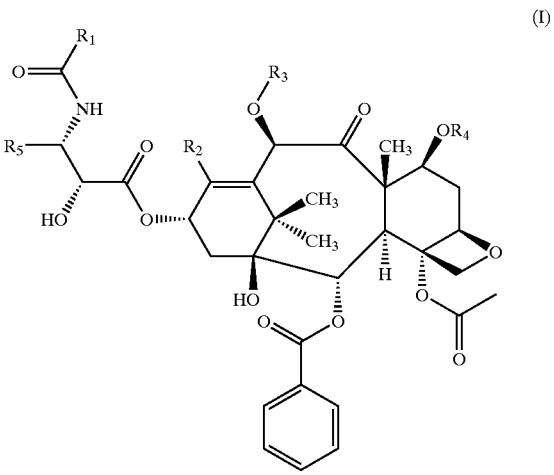

wherein:
R$_1$ is selected from among phenyl, t-butoxy, isopropyloxy, propyloxy, —C(CH$_3$)═CH—CH$_3$, 2-naphthyl, 4-hydroxyphenyl, 4-methoxyphenyl, 4-fluorophenyl, 2-methyl-1-propenyl, cyclopropyl, 3-furanyl, 3-thioethyl and 2-propenyl;

$R_2$ is one of acetyl, —$CH_3$, —$CH_2CH_3$ and —CHO;

$R_3$ is selected from among acetyl, H and $C_{1-6}$ alkyl;

$R_4$ is selected from among H, F, $C_{1-6}$ alkyl, —C(O)—$CH_2CH_2CH_2CH_2CH_3$, —$CH_2SCH_3$, —$SiEt_3$, —$CH_2OP(O)(OCH_2Ph)_2$, $CH_3CH_2C(O)$—, —$CH_2O$(CO)$CH_2N(CH_2CH_2)_2NCH_3$, —$CH_2O$(CO)$CH_2N(CH_2CH_3)_2$, —$C(O)CH_2N(CH_3)_2$, —$C(O)CH(CH_3)NHCOOC(CH_3)_3$; and $R_5$ is selected from among phenyl, 4-methoxyphenyl, 3,4-dimethoxyphenyl, 4-fluorophenyl, 4-trifluorotoluene, 2-furanyl, 2-thienyl, phenylethene, 2-furanyl—CH=CH—, $(CH_3)_2CHCH_2$—, $C_6H_{11}$—$CH_2$—, $(CH_3)_2CH$—, $PhCH_2CH_2$—, $C_6H_{11}$—$CH_2CH_2$—, $CH_3CH_2CH_2$—, 4—Cl-phenyl-, 2-fluorophenyl-, 3-fluoro-phenyl- and 4-$CH_3$-phenyl-.

In more preferred aspects of the invention, the taxane is paclitaxel which has the structure:

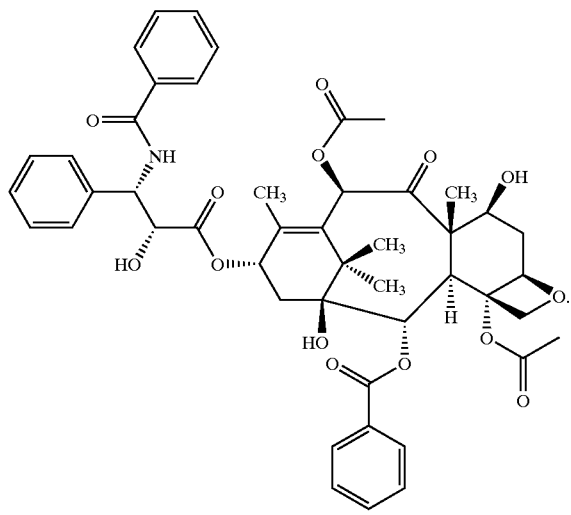

One of the keys to the process of the present invention is the use of Bsmoc, e.g. 1,1 dioxobenzo-[b]thiophene-2-ylmethyloxycarbonyl, and related protecting reagents as well as blocked amino acids including the same. Such reagents are of formula (II)

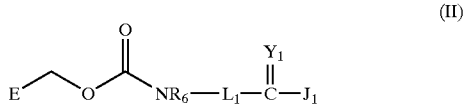

(II)

wherein:

E is one of:

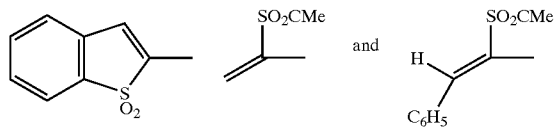

$L_1$ is a bifunctional group;

$Y_1$ is selected from among O, S or $NR_7$;

$R_6$ and $R_7$ are independently selected from the group consisting of hydrogen, $C_{1-6}$ alkyls, $C_{3-19}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy; and $J_1$ is selected from the group consisting of OH and leaving groups.

Among the protected amino acids, the most preferable is

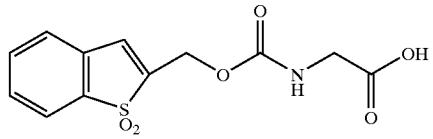

which is available from Morre-Tec Industries, Inc. of Union, N.J.

In alternative embodiments, the

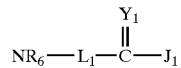

portion of formula (II) and the

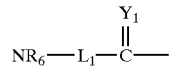

of formula (I) include amino acid residues. Such residues can be selected from among naturally-occurring L-amino acids and D-amino acids. A non-limiting list of such amino acids include alanine, valine, leucine, isoleucine, glycine, serine, threonine, methionine, cysteine, phenylalanine, tyrosine, tryptophan, aspartic acid, glutamic acid, lysine, arginine, histidine and proline.

In a still further aspect of this embodiment,

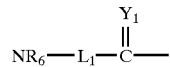

can be a peptide residue comprising from about 2 to about 10 amino acids. When $L_1$ includes a peptide, the peptide ranges in size, for instance, from about 2 to about 10 amino acid residues. In one preferred embodiment, the peptide is Gly-Phe-Leu—. Alternatively, glycine can be added to the aforementioned tripeptide after leucine to form a 4 residue peptide.

The amino acid residues are preferably of the formula

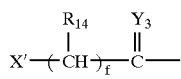

wherein X' is O, S or $NR_{15}$, $Y_3$ is O, S or $NR_{16}$ and $R_{14}$, $R_{15}$ and $R_{16}$ are independently selected from the same group as that which defines $R_6$ but each is preferably H or lower alkyl; and f is a positive integer from about 1 to about 10, and is preferably 1.

Derivatives and analogs of the naturally occurring amino acids, as well as various art-known non-naturally occurring amino acids (D or L), hydrophobic or non-hydrophobic, are also contemplated to be within the scope of the invention. Simply by way of example, amino acid analogs and derivates include: 2-aminoadipic acid, 3-amino-adipic acid, beta-alanine, beta-aminopropionic acid, 2-aminobutyric acid, 4-amino-butyric acid, piperidinic acid, 6-aminocaproic acid, 2-aminoheptanoic acid, 2-aminoisobutyric acid, 3-aminoisobutyric acid, 2-aminopimelic acid, 2,4-diaminobutyric acid, desmosine, 2,2-diaminopimelic acid, 2,3-diaminopropionic acid, n-ethylglycine, N-ethylasparagine, 3-hydroxyproline, 4-hydroxyproline, isodesmosine, allo-isoleucine, N-methylglycine, sarcosine, N-methylisoleucine, 6-N-methyl-lysine, N-methylvaline, norvaline, norleucine, ornithine, and others too numerous to mention, that are listed in 63 Fed. Reg., 29620, 29622, incorporated by reference herein.

Short peptides are, for example, peptides ranging from 2 to about 10, or more, amino acid residues, as mentioned supra.

Within the various formulae set forth above, $L_1$ and $L_2$ are described as being independently selected bifunctional linkers. A non-limiting list of suitable groups include —(CH$_2$CH$_2$O)$_n$(CH$_2$)$_n$NR$_{10}$—,
—(CH$_2$CH$_2$O)$_n$—,
—(C$_{13}$R$_{12}$)$_n$O—,
—C(O)(CR$_{11}$R$_{12}$)$_n$NHC(O)(CR$_{13}$R$_{14}$)$_q$NR$_{10}$—,
—C(O)O(CH$_2$)$_n$O—,
—C(O)(CR$_{11}$R$_{12}$)$_n$NR$_{10}$—,
—C(O)NH(CH$_2$CH$_2$O)$_n$(CH$_2$)$_n$NR$_{10}$—,
—C(O)O—(CH$_2$CH$_2$O)$_n$NR$_{10}$—,
—C(O)NH(CR$_{11}$R$_{12}$)$_n$O—,
—C(O)O(CR$_{11}$R$_{12}$)$_n$O—,
—C(O)NH(CH$_2$CH$_2$O)$_n$—,

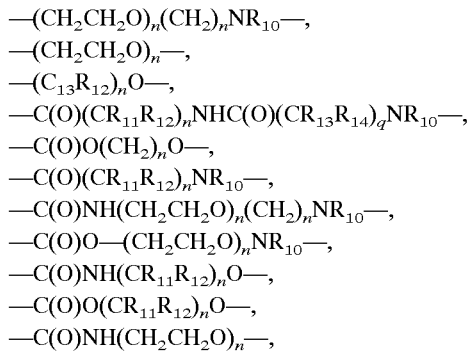

wherein
$R_{10-12}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

$R_{13}$ is selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy, NO$_2$, haloalkyl and halogen; and n and q are independently selected positive integers.

Secondary Amine Deprotecting Reagents

The process of the present invention includes deprotecting the blocked 2'-amino acid or peptide found on the taxane. Deprotection is preferably carried out with a secondary amine such as piperidine, a piperidine-containing secondary amine or 4-piperidinopiperidine. Such reagents are available from commercial from suppliers such as Aldrich. The deprotection is also preferably carried out under substantially anhydrous conditions. Care must be taken therefore to be assured that the liquid piperidine is dry as the presence of moisture is believed to contribute to decomposition of the desired 2'-amino acid taxane. For ease of carrying out the inventive process, the use of a solid secondary amine such as piperidinopiperidine is especially preferred.

Reaction Conditions a) Condensing Agents

The methods of the present invention further include reacting the taxane and protected amino acid in the presence of a condensing agent. A non-limiting list of suitable condensing agents include 1,3-diisopropylcarbodiimide (DIPC), 1,-(3-dimethyl aminopropyl)-3-ethyl carbodiimide hydrochloride (EDC), dialkyl carbodiimide, Mukaiyama reagents (e.g. 2-halo-1-alkyl-pyridinium halides) or propane phosphonic acid cyclic anhydride (PPACA), N-ethoxycarbonyl-2-ethoxy-1,2-dihydroquinoline (EEDQ), dicyclohexylcarbodiimide (DCC) and mixtures thereof Others will be apparent to those of ordinary skill. The condensing agent is preferably 1(3-dimethyl amino-propyl) 3-ethylcarbodiimide hydrochloride (EDC).

b) Bases

The processes of the invention are preferably carried out in the presence of a base. Suitable bases are tertiary amine bases such as those in the dialkylaminopyridine class. Preferred bases include dimethylaminopyridine (DMAP) and diethylaminopyridine. More preferable is dimethylaminopyridine (DMAP).

c) Reaction Temperature

The methods of the invention are preferably carried out at a temperature of from about 0 to about 30° C., and more preferably at a temperature of from about 10 to about 25° C.

d) The Deprotecting Step

One of the keys to the present invention is the deprotection of the 2'-protected amino acid taxane. As stated above, it is preferred that about equimolar amounts of a secondary amine (with respect to the protected amino acid taxane) is used.

Polymer Attachment

In alternative aspects of the invention, the methods of the invention further include reacting a compound of formula (IV) with an activated substantially non-antigenic polymer of formula (Va) or (Vb) under conditions sufficient to form a polymer conjugate corresponding to formula (VIa) and (VIb)respectively. Preferred substantially non-antigenic polymers comprise a polyalkylene oxide residue such as a polyethylene glycol residue.

$R_8$ is preferably includes a water soluble polymer residue which is preferably substantially non-antigenic such as a polyalkylene oxide (PAO) and, more preferably, a polyethylene glycol such as PEG. For purposes of illustration and not limitation, the polyethylene glycol (PEG) residue portion of R8 can be selected from among:

J$_3$—O—(CH$_2$CH$_2$O)$_x$—
J$_3$—O—(CH$_2$CH$_2$O)$_x$—CH$_2$C(O)—O—, $J_3$—O—$(CH_2CH_2O)_x$—$CH_2CH_2NR_{18}$—, $J_3$—O—$(CH_2CH_2O)_x$—$CH_2CH_2SH$—,

—OC(O)$CH_2$—O—$(CH_2CHO)_x$—$CH_2C(O)$—O—,

—$NR_{15}CH_2CH_2$—O—$(CH_2CH_2O)_x$—$CH_2CH_2NR_{18}$— and

—$SHCH_2CH_2$—O—$(CH_2CH_2O)_x$—$CH_2CH_2SH$— wherein x is the degree of polymerization, $R_{18}$ is selected from among hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy and J is a capping group i.e. a group which is found on the terminal of the polymer and, in some aspects, can be selected from any of $NH_2$, OH, SH, $CO_2H$, $C_{1-6}$ alkyls or other PEG terminal activating groups, as such groups are understood by those of ordinary skill. In one particularly preferred embodiment, $R_8$ is selected from among $CH_3$—O—$(CH_2CH_2O)_x$—, $CH_3$—O—$(CH_2CH_2O)_x$—$CH_2C(O)$—O—, $CH_3$—O—$(CH_2CH_2O)_x$—$CH_2CH_2NH$— and $CH_3$—O—$(CH_2CH_2O)_x$—$CH_2CH_2SH$—, PEG is generally represented by the structure:

$$O-(OCH_2CH_2O)_x-$$

and $R_8$ preferably comprises a residue corresponding thereto.

The degree of polymerization for the polymer (x) can be from about 10 to about 2,300. This represents the number of repeating units in the polymer chain and is dependent on the molecular weight of the polymer. Also useful are polypropylene glycols, branched PEG derivatives such as those described in commonly-assigned U.S. Pat. No. 5,643,575 (the '575 patent), "star-PEG's" and multi-armed PEG's such as those described in Shearwater Corporation's 2001 catalog "Polyethylene Glycol and Derivatives for Biomedical Application". The disclosure of each of the foregoing is incorporated herein by reference. The branching afforded by the '575 patent allows secondary or tertiary branching from the bicine group as a way of increasing polymer loading on a biologically active molecule or enzyme from a single point of attachment. It will be understood that the water-soluble polymer can be functionalized for attachment to the bifunctional linkage groups if required without undue experimentation.

Although PAO's and PEG's can vary substantially in weight average molecular weight, preferably, $R_8$ has a weight average molecular weight of from about 20,000 to about 100,000 Da in most aspects of the invention.

The polymeric substances included herein are preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

In a further embodiment, and as an alternative to PAO-based polymers, $R_8$ is selected from among one or more effectively non-antigenic materials such as dextran, polyvinyl alcohols, carbohydrate-based polymers, hydroxypropylmeth-acrylamide (HPMA), polyalkylene oxides, and/or copolymers thereof. See also commonly-assigned U.S. Pat. No, 6,153,655, the contents of which are incorporated herein by reference. It will be understood by those of ordinary skill that the same type of activation is employed as described herein as for PAO's such as PEG. Those of ordinary skill in the art will further realize that the foregoing list is merely illustrative and that all polymeric materials having the qualities described herein are contemplated and that other polyalkylene oxide derivatives such as the polypropylene glycols, etc. are also contemplated.

Leaving Groups

In those aspects where $J_1$ or $J_2$ is a leaving group, suitable moieties include, without limitation, groups such as N-hydroxybenzotriazolyl, halogen, N-hydroxyphthalimidyl, p-nitrophenoxy, imidazolyl, N-hydroxysuccinimidyl; thiazolidinyl thione, O-acyl ureas or

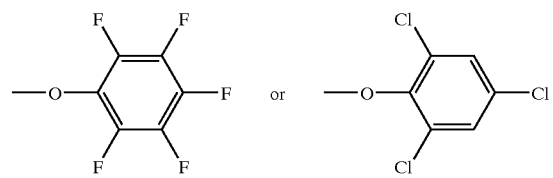

other suitable leaving groups will be apparent to those of ordinary skill.

For purposes of the present invention, leaving groups are to be understood as those groups which are capable of reacting with a nucleophile found on the desired target, i.e. the 2'—OH of a taxane.

EXAMPLES

Figure 2:
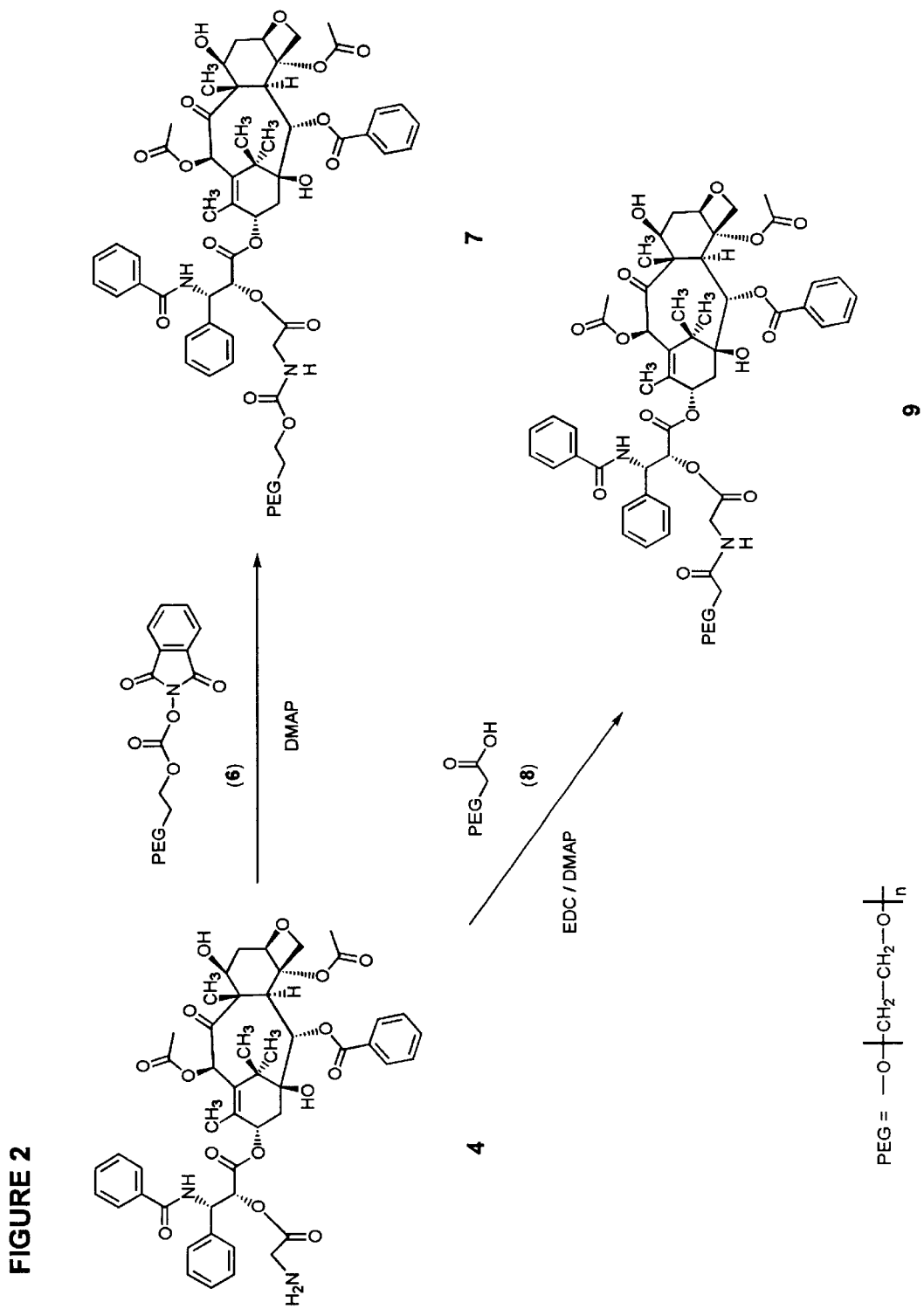

The following examples serve to provide further appreciation of the invention but are not meant in any way to restrict the effective scope of the invention. The underlined and bold-faced numbers recited in the Examples correspond to those shown in the FIGS. 1–2.

General Procedures. All reactions were run under an atmosphere of dry nitrogen or argon. Commercial reagents were used without further purification. All PEG compounds were dried under vacuum or by azeotropic distillation from toluene prior to use. $^1$H and $^{13}$C NMR spectra were obtained using a Varian Mercury® 300 NMR spectrometer and deuterated chloroform as the solvent unless otherwise specified. Chemical shifts (δ) are reported in parts per million (ppm) downfield from tetramethylsilane (TMS).

HPLC method. The reaction mixtures and the purity of intermediates and final products were monitored by a Beckman Coulter System Gold® HPLC instrument employing a ZOBAX® 300 SB C-8 reversed phase column (150×4.6 mm) or a Phenomenex Jupiter® 300A C18 reversed phase column (150×4.6 mm) with a multi-wavelength UV detector, using a gradient of 10–90% of acetonitrile in 0.5% trifluoroacetic acid (TFA) at a flow rate of 1 mL/min.

Example 1

Compound 3. To a solution of 1 (1.00 g, 1.17 mmol), 2 (0.375 g, 1.34 mmol) and dimethylaminopyridine (DMAP, 0.043 g, 0.35 mmol) in methylene chloride (DCM, 100 mL)

cooled to 10° C. was added 1-[3-(dimethylamino)propyl]-3-ethylcarbodiimide hydrochloride (EDC, 0.336 g, 1.75 mmol) and the solution continuously stirred at 10° C. for 50 min before it was warmed to room temperature and stirred for another 30 min. The reaction mixture was washed with 0.1 M HCl (2×50 mL), water (50 mL), dried (MgSO$_4$), filtered and the solvent evaporated under reduced pressure to give 3 (1.20 g, 1.05 mmol, 90%). $^{13}$C NMR (67.8 MHz, CDCl$_3$) δ 203.49, 170.95, 169.70, 168.72, 167.51, 166.98, 166.80, 155.31, 142.33, 138.82, 136.80, 136.53, 133.64, 133.57, 132.73, 131.87, 130.50, 129.78, 128.97, 128.53, 127.13, 126.82, 126.58, 125.31, 121.43, 84.36, 81.05, 79.05, 76.39, 75.57, 75.00, 74.85, 72.04, 58.47, 57.17, 52.91, 45.68, 43.18, 42.75, 35.57, 26.84, 22.74, 20.91, 14.89, 9.69; $^1$H NMR (300.07 MHz, CDCl$_3$) δ 1.14 (s, 3H), 1.22 (s, 3H), 1.68 (s, 3H), 1.83 (s, 2H), 1.90 (s, 3H), 2.22 (s, 3H), 2.30 (s, 1H), 2.43 (s, 3H), 2.56 (s, H), 3.79(d, J=6.3 Hz, H), 4.04 (m, H), 4.12 (d, J=5.7MHz, H), 4.19(d, J=8.1 Hz, H), 4.30 (d, J=8.4 Hz, H), 4.42 (m, H), 4.96 (d, J=9.6 Hz, H), 5.06 (s, H), 5.56 (m, H), 5.66 (d, J=4.2 Hz, H), 6.00 (m, H), 6.22 (t, J=8.4 Hz, H), 6.29 (s, H), 7.08 (s, H), 7.15 (d, J=8.7 Hz, H), 7.30–7.70 (m, 16H), 7.77 (d, J=8.4 Hz, H), 8.13 (d, J=7.5 Hz, H).

Example 2

Compound 4. To a solution of 3 (0.070 g, 0.0642 mmol) in DCM (5 mL) was added piperidine (6.3 μL, 0.0642 mmol) and stirred for 2 hrs at room temperature. The solution was concentrated to about 1 mL by rotary evaporation and hexane (10 ml) added to precipitate the product. The resulting mixture was centrifuged and supernatant decanted. The hexane wash was repeated twice and the final residue was dried in desiccator over phosphorus pentoxide to give 4 (0.030 g, 0.0327 mmol, 51%). $^{13}$C NMR (67.8 MHz, CDCl$_3$) δ 203.51, 173.24, 171.02, 169.64, 167.76, 166.93, 166.81, 142.41, 136.67, 133.55, 133.46, 132.77, 131.92, 130.09, 129.06, 129.00, 128.62, 128.44, 126.97, 126.38, 84.39, 81.06, 79.08, 76.42, 75.55, 75.08, 74.27, 72.07, 71.93, 58.52, 54.72, 52.78, 45.63, 43.65, 43.21, 35.62, 26.87, 26.02, 22.78, 22.19, 20.91, 14.88, 9.70; $^1$H NMR (300.07 MHz, CDCl$_3$) δ 1.14 (s, 3H), 1.23 (s, 3H), 1.68 (s, 3H), 1.95 (s, 3H), 2.22 (s, 3H), 2.46 (s, 3H), 2.58 (s, H), 3.82 (d, J=6.6 Hz, H), 4.20 (d, J=8.7 Hz, H), 4.31 (d, J=8.4 Hz, H), 4.47 (m, H), 4.97 (d, J=9.3 Hz, H), 5.55 (d, J=3.3 Hz, H), 5.68 (d, J=6.9 Hz, H), 6.00 (d, J=3.3 Hz, H), 6.25 (t, J=8.4 Hz, H), 6.30 (s, H), 6.96 (s, H), 6.99 (d, J=8.7 Hz, H), 7.30–7.70 (m, 16H), 7.73 (d, J=4.2 Hz, H), 8.13 (d, J=6.9 Hz, H).

Example 3

Compound 7. To a solution of 3 (2.10 g, 1.85 mmol) in DCM (200 mL) was added 4-piperidino piperidine (0.281 g, 0.167 mmol) and stirred for 3 hrs at room temperature. To the reaction mixture was then added 6 (15.0 g, 0.375 mmol) and DMAP (0.186 g, 1.52 mmol) and stirring continued for 12 hrs. The solution was washed with 0.1 M HCl (2×200 mL) and water (200 mL), dried (MgSO$_4$), filtered, the solvent evaporated under reduced pressure and the residue crystallized from dimethylformamide/isopropyl alcohol (DMF/IPA=1:4, 300 mL) to give 7 (12.88 g, 0.284 mmol, 82%). $^{13}$C NMR (67.8 MHz, CDCl$_3$) δ 203.00, 170.35, 169.16, 168.89, 167.15, 166.64,166.20, 156.02, 141.93, 136.31, 133.12, 132.27, 131.35, 129.64, 128.74, 128.55, 128.19, 128.04, 126.81, 126.27, 83.90, 80.56, 78.45, 75.89, 75.08, 74.56, 74.12, 63.90, 57.98, 52.58, 45.27, 42.78, 35.30, 35.16, 26.42, 22.33, 21.69, 20.51, 14.43, 9.28.

Example 4

Compound 9. The procedure of Compound 7 is followed, except that PEG-COOH (8) (15.0 g, 0.375 mmol) is used with 2 equivalents of EDC in place of 6 to form an amide-linked PEG conjugate 9. The structure of (9) is confirmed by NMR.

Example 5 (Comparative)

An alternative method of making Compound 11 was pursued with reference to reaction scheme 3 provided below. To a solution of Fmoc-Glycine (1.95 g, 6.44 mmol), DMAP (3.1 g, 25.4 mmol), and 1 (5.0 g, 5.88 mmol) in anhydrous DCM (500 mL) chilled to −8 ° C. for 30 min. was added solid EDC (2.5 g, 13.0 mmol) in one portion and the reaction mixture stirred at −8° C. for 30 min. The reaction was allowed to warm up to room temperature and continuously stirred for 6 h. The solution was washed with 0.1 N HCl (300 mL) and water (300 mL) and the organic layer was dried over anhydrous magnesium sulfate, filtered and the solvent evaporated to give 11 (6.3 g, 5.56 mmol, 95%). $^1$H NMR (270 MHz, CDCl$_3$) δ 8.12 (d, J=7.3 Hz, 1H), 7.73 (t, J=7.2 Hz, 2H), 7.45–7.61 (m, 2H), 7.28–7.43 (m, 4H), 7.02 (d, J=9.2 Hz, 1H), 6.28 (s, 1H), 6.23 (t, J=8.9 Hz, 1H), 5.97 (d & d, J$_1$=8.9 Hz, J$_2$=3.0 Hz, 1H), 5.67 (d, J=6.9 Hz, 1H), 5.52 (d, J=3.0 Hz, 1H), 5.36 (t, J=5.6 HZ, 1H), 4.95 (d, J=8.2 HZ, 1H), 4.28–4.45 (m, 2H) 4.14 (d & d, J$_1$=30.0 Hz, J$_2$=8.6 Hz, 2H), 3.79 (d, J=6.9 Hz, 1H), 2.50–2.59 (m, 1H), 2.43 (s, 1H), 2.20 (s, 1H), 1.91 (s, 2H), 1.67 (s, 1H), 1.21 (s, 1H), 1.12 (s, 1H); $^{13}$C NMR (67.8 MHz, CDCl$_3$) δ 203.7, 171.2, 169.8, 169.2, 167.6, 167.2, 166.9, 156.2, 143.6, 142.4, 141.2, 136.6, 133.6, 133.5, 132.8, 132.0, 130.2, 129.1, 128.7, 127.7, 127.1, 127.0, 126.5, 124.9, 120.0, 84.4, 81.0, 79.0, 75.5, 75.0, 74.8, 72.1, 67.3, 58.5, 52.8, 46.9, 45.6, 43.1, 35.5, 26.8, 22.7, 22.1, 20.8, 14.8, 9.6.

Compound 4. A solution of 11 (0.843 g, 0.744 mmol) and DMAP (2.727 g, 22.32 mmol) in anhydrous chloroform (150 mL) was refluxed for 1 h. The reaction was monitored by HPLC and found about 70% free taxol formed along with compound 4. The reaction had to be abandoned due to substantial decomposition of desired product.

Scheme 3: Preparation of Gly-Paclitaxel using Fmoc protecting group

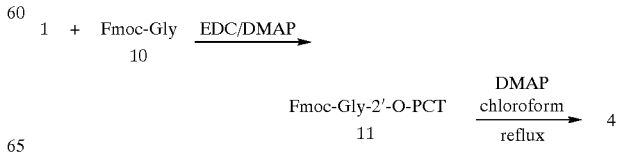

We claim:
1. A method of preparing a 2'-substituted taxane, comprising:
a) reacting a taxane of the formula (I)

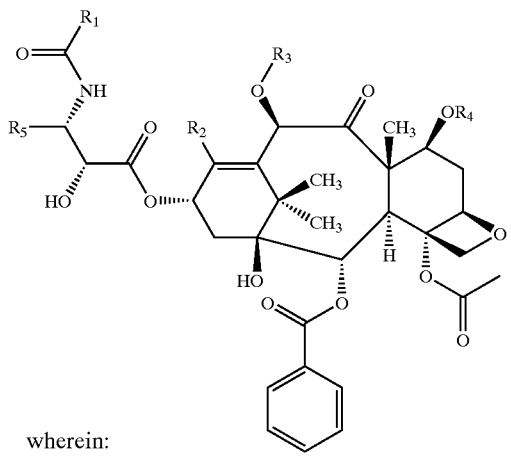

wherein:
R$_1$ is selected from the group consisting of phenyl, t-butoxy, isopropyloxy, propyloxy, —C(CH$_3$)=CH—CH$_3$, 2-naphthyl, 4-hydroxyphenyl, 4-methoxyphenyl, 4-fluorophenyl, 2-methyl-1-propenyl, cyclopropyl, 3-furanyl, 3-thioethyl and 2-propenyl;
R$_2$ is selected from the group consisting of acetyl, —CH$_3$, —CH$_2$CH$_3$ and —CHO;
R$_3$ is selected from the group consisting of acetyl, H and C$_{1-6}$ alkyl;
R$_4$ is selected from among H, F, C$_{1-6}$ alkyl, —C(O)—CH$_2$CH$_2$CH$_2$CH$_2$CH$_3$, —CH$_2$SCH$_3$, —SiEt$_3$, —CH$_2$OP(O)(OCH$_2$Ph)$_2$, CH$_3$CH$_2$C(O)—, —CH$_2$O(CO)CH$_2$N(CH$_2$CH$_2$)$_2$NCH$_3$, —CH$_2$O(CO)CH$_2$N(CH$_2$CH$_3$)$_2$, —C(O)CH$_2$N(CH$_3$)$_2$, —C(O)CH(CH$_3$)NHCOOC(CH$_3$)$_3$; and
R$_5$ is selected from the group consisting of phenyl, 4-methoxyphenyl, 3,4-dimethoxyphenyl, 4-fluorophenyl, 4-triflourotoluene, 2-furanyl, 2-thienyl, phenylethene, 2-furanyl-CH=CH—, (CH$_3$)$_2$CHCH$_2$—, C$_6$H$_{11}$—CH$_2$—, (CH$_3$)$_2$CH—, PhCH$_2$CH$_2$—, C$_6$H$_{11}$—CH$_2$CH$_2$—, CH$_3$CH$_2$CH$_2$—, 4—Cl-phenyl-, 2-fluorophenyl-, 3-fluoro-phenyl- and 4—CH$_3$-phenyl- with a compound of formula (II)

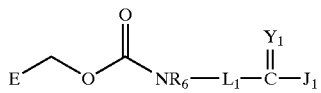

wherein:
E is a member of the group consisting of

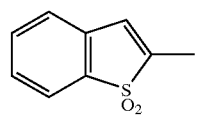 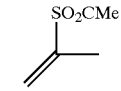 and 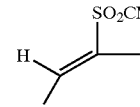

L$_1$ is a bifunctional group;
Y$_1$ is selected from among O, S or NR$_7$;
R$_6$ and R$_7$ are independently selected from the group consisting of hydrogen, C$_{1-6}$ alkyls, C$_{3-19}$ branched alkyls, C$_{3-8}$ cycloalkyls, C$_{1-6}$ substituted alkyls, C$_{3-8}$ substituted cycloalkyls, aryls, substituted aryls, aralkyls, C$_{1-6}$ heteroalkyls, substituted C$_{1-6}$ heteroalkyls, C$_{1-6}$ alkoxy, phenoxy and C$_{1-6}$ heteroalkoxy; and
J$_1$ is selected from the group consisting of OH and leaving groups; under conditions sufficient to form a blocked intermediate of the formula (III)

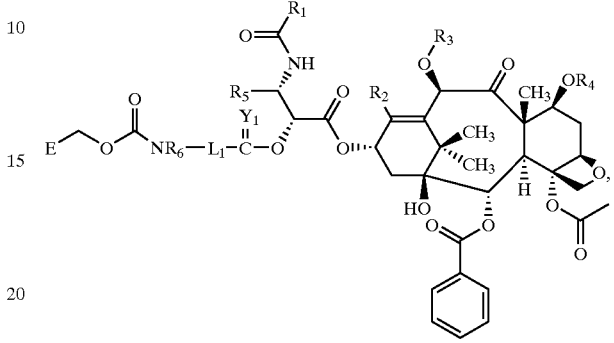

and b) deprotecting said blocked intermediate with about an equimolar amount of a secondary amine under conditions sufficient to form a compound of formula (IV):

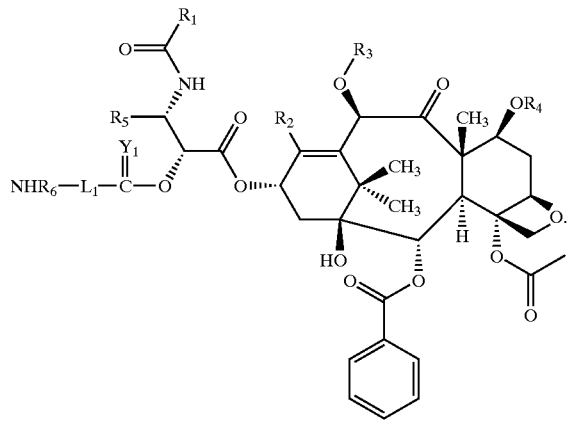

2. The method of claim 1, wherein said taxane comprises the formula:

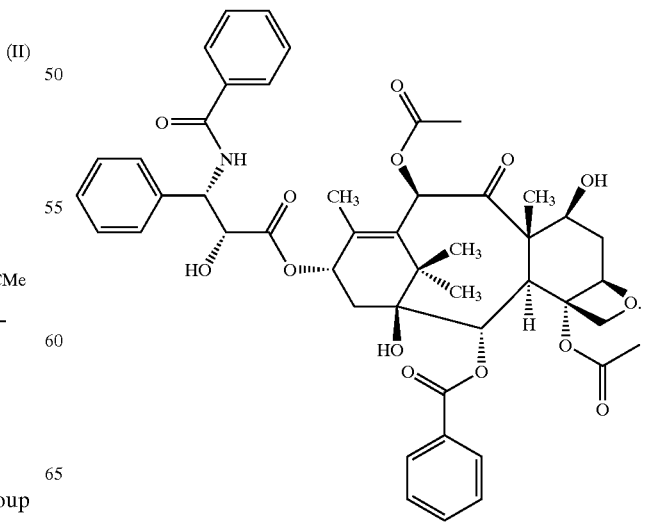

3. The method of claim 2, wherein

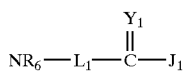

of said compound of formula (II) comprises an amino acid residue.

4. The method of claim 1, wherein said compound of formula (II) is

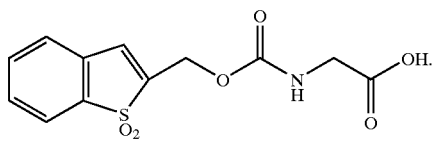

5. The method of claim 1, wherein said reacting is carried out in the presence of a condensing agent.

6. The method of claim 5, wherein said condensing agent is selected from the group consisting of 1,3-diisopropylcarbodiimide (DIPC), 1-(3-dimethyl aminopropyl)-3-ethylcarbodiimide hydrochloride (EDC), dialkyl carbodiimide, Mukaiyama reagents (e.g. 2-halo-1-alkyl-pyridinium halides) or propane phosphonic acid cyclic anhydride (PPACA), N-ethoxycarbonyl-2-ethoxy-1,2-dihydroquinoline (EEDQ), dicyclohexylcarbodiimide (DCC) and mixtures thereof.

7. The method of claim 6, wherein said condensing agent is 1(3-dimethylaminopropyl) 3-ethylcarbodimide hydrfochloride (EDC).

8. The method of claim 1, wherein said reacting is carried out in the presence of a base.

9. The method of claim 8, wherein said base is a tertiary amine base.

10. The method of claim 8, wherein said tertiary amine base is a dialkylaminopyridine.

11. The method of claim 10, wherein said dialkylaminopyridine is selected from the group consisting of dimethylaminopyridine (DMAP) and diethylaminopyridine.

12. The method of claim 11, wherein said dialkylaminopyridine is dimethylaminopyridine (DMAP).

13. The method of claim 1, wherein said reacting is carried out at a temperature of from about 0 to about 30° C.

14. The method of claim 13, wherein said reacting is carried out a temperature of from about 10 to about 25° C.

15. The method of claim 1, wherein said secondary amine is a piperidine.

16. The method of claim 15, wherein said piperidine is piperidino-piperadine.

17. The method of claim 5, wherein said wherein said condensing agent is 1-(3-dimethylaminopropyl) 3-ethylcarbodiimide hydrochloride (EDC), said secondary amine is dimethylaminopyridine (DMAP) and said deblocking is carried out with piperidino-piperadine.

18. The method of claim 2, wherein said compound of formula (II) is

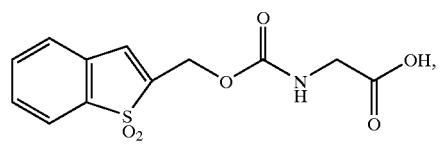

said reacting step 1a) is carried out in the presence of a condensing agent comprising 1-,(3-dimethyl aminopropyl) 3-ethyl carbodimide, said secondary amine is dimethylaminopyridine (DMAP) and said deprotecting step 1b) is carried out with piperidino-piperadine.

19. The method of claim 1, further comprising reacting said compound of formula (IV) with an activated substantially non-antigenic polymer under conditions sufficient to form a polymer conjugate thereof.

20. The method of claim 19, wherein said substantially non-antigenic polymer comprises a polyethylene glycol residue.

21. The method of claim 19, wherein said polymer conjugate is selected from the group consisting of formula (VIa):

and formula (VIb):

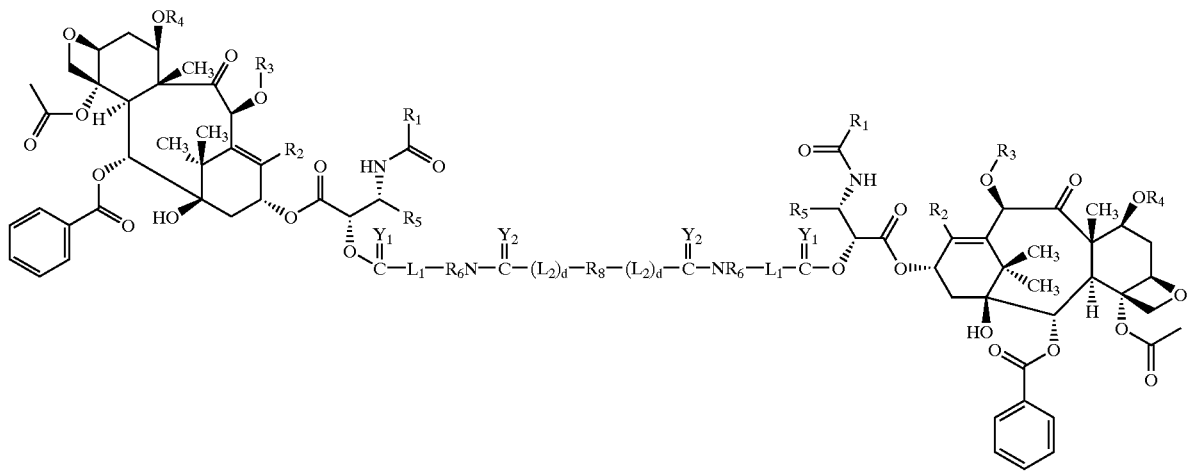

wherein
- $R_8$ is a residue of a substantially non-antigenic polymer;
- $L_2$ is a bifunctional linker;
- $Y_2$ is selected from among O, S and $R_{7a}$ where $R_{7a}$ is selected from the group consisting of hydrogen, $C_{1-6}$ alkyls, $C_{3-19}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ hetero-alkyls, $C_{1-6}$ alkoxy, phenoxy and $C_{1-6}$ heteroalkoxy;
- d is zero or one; and
- $J_2$ is OH or a leaving group.

22. The method of claim 19, wherein said polyethylene glycol has a weight average molecular weight of from about 20,000 Da to about 100,000 Da.

23. The method of claim 1, wherein

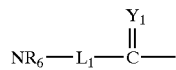

is an amino acid residue selected from the group consisting of naturally-occurring L-amino acids and D-amino acids.

* * * * *

UNITED STATES PATENT AND TRADEMARK OFFICE
CERTIFICATE OF CORRECTION

PATENT NO. : 6,649,778 B1
DATED : November 18, 2003
INVENTOR(S) : Zhao, H. et al.

It is certified that error appears in the above-identified patent and that said Letters Patent is hereby corrected as shown below:

Column 17,
Line 31, "3-ethylcarbodimide hydrfochloride" should read -- 3-ethylcarbodiimide hydrochloride --;

Column 18,
Line 5, "out a" should read -- out at a --;
Line 11, "wherein said wherein said" should read -- wherein said --; and
Line 30, "carbodimide" should read -- carbodiimide --.

Signed and Sealed this

Fifth Day of October, 2004

JON W. DUDAS
*Director of the United States Patent and Trademark Office*